(12) United States Patent
Lorca et al.

(10) Patent No.: US 11,602,553 B2
(45) Date of Patent: Mar. 14, 2023

(54) COMPOSITION OF LACTOBACILLUS AND BERRY EXTRACT

(71) Applicant: UNIVERSITY OF FLORIDA RESEARCH FOUNDATION, INCORPORATED, Gainesville, FL (US)

(72) Inventors: Graciela Liliana Lorca, Gainesville, FL (US); Claudio F. Gonzalez, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 17/256,388

(22) PCT Filed: Jun. 27, 2019

(86) PCT No.: PCT/US2019/039450
§ 371 (c)(1),
(2) Date: Dec. 28, 2020

(87) PCT Pub. No.: WO2020/006198
PCT Pub. Date: Jan. 2, 2020

(65) Prior Publication Data
US 2021/0145905 A1 May 20, 2021

Related U.S. Application Data

(60) Provisional application No. 62/690,627, filed on Jun. 27, 2018.

(51) Int. Cl.
| | | |
|---|---|---|
| A61K 35/747 | (2015.01) | |
| A61K 9/00 | (2006.01) | |
| A61K 9/19 | (2006.01) | |
| A61K 47/10 | (2017.01) | |
| A61K 47/46 | (2006.01) | |

(52) U.S. Cl.
CPC .......... *A61K 35/747* (2013.01); *A61K 9/0053* (2013.01); *A61K 9/19* (2013.01); *A61K 47/10* (2013.01); *A61K 47/46* (2013.01)

(58) Field of Classification Search
None
See application file for complete search history.

(56) References Cited

U.S. PATENT DOCUMENTS

| | | | | |
|---|---|---|---|---|
| 9,474,773 | B2 * | 10/2016 | Neu | ............ A61P 1/14 |
| 9,987,313 | B2 * | 6/2018 | Lorca | ............ A61P 1/14 |
| 10,925,907 | B2 * | 2/2021 | Lorca | ............ A61K 35/747 |
| 2016/0193306 | A1 | 7/2016 | Rabovsky et al. | |
| 2018/0028582 | A1 * | 2/2018 | Bel-Rhlid | ............ A61K 36/53 |
| 2019/0336548 | A1 * | 11/2019 | Lorca | ............ A23L 33/135 |

FOREIGN PATENT DOCUMENTS

| | | | |
|---|---|---|---|
| WO | WO 2007/009187 | * | 1/2007 |
| WO | WO 2010/096550 | * | 8/2010 |
| WO | 2020006198 A1 | | 1/2020 |

OTHER PUBLICATIONS

Jakesevic M. et al. Effects of Bilberry in Combination with Lactic Acid Bacteria on Intestinal Oxidative Stress . . . J of Agricultural and Food Chemistry 61(14)3468-3478 Apr. 10, 2013. (Year: 2013).*
Kling, D. et al. The Synergistic Contribution of Lactobacillus and Dietary Phytophenols in Host Health. Probiotics and Prebiotics in Human Nutrition and Health InTech Pub. pp. 83-114, 2016. (Year: 2016).*
Bhat, Ravish et al., "Lactobacillus plantarum mediated fermentation of *Psidium guajava* L. fruit extract", Journal of Bioscience and Bioengineering, 2015, vol. 119, No. 4, pp. 430-432.
Bravo-Ferrada, Barbara Mercedes et al., "Effect of protective agents and previous acclimation on ethanol resistance of frozen and freeze-dried Lactobacillus plantarum strains", Cryobiology, 2015, vol. 71, pp. 522-528.
Bustamante, Mariela et al., "Effective Lactobacillus plantarum and Bifidobacterium infantis encapsulation with chia seed (*Salvia hispanica* L.) and flaxseed (*Linum usitatissimum* L.) mucilage and soluble protein by spray drying", Food Chemistry, 2017, vol. 216, pp. 97-105.
Correa-Betanzo, J. et al., "Stability and biological activity of wild blueberry (*Vaccinium angustifolium*) polyphenols during simulated in vitro gastrointestinal digestion", Food Chemistry, 2014, vol. 165, pp. 522-531.
Correa-Betanzo, Julieta et al., "Complex Formation of Blueberry (*Vaccinium angustifolium*) Anthocyanins during Freeze-Drying and Its Influence on Their Biological Activity", J. Agric. Food Chem., 2015, vol. 63, pp. 2935-2946.
Costa, Mayra Garcia Maia et al., "Synbiotic Amazonian palm berry (açai, Euterpe oleracea Mart.) ice cream improved Lactobacillus rhamnosus GG survival to simulated gastrointestinal stress", Food Funct., 2017, vol. 8, 731-740. Dong, Li Mei et al., "Phenolics from Mikania micrantha and Their Antioxidant Activity",Molecules, 2017, vol. 22, No. 1140, 10 pages.

(Continued)

*Primary Examiner* — Ralph J Gitomer
(74) *Attorney, Agent, or Firm* — Timothy H. Van Dyke; Wolter, Van Dyke, Davis, PLLC

(57) ABSTRACT

A composition is provided herein directed to a mixture of one or more *Lactobacillus* sp. and a phenolic compound. In a specific embodiment, disclosed is a *Lactobacillus*/phenol mixture that has been lyophilized to form a *Lactobacillus*/phenol lyophilized mixture. The *Lactobacillus*/phenol mixture of *Lactobacillus*/phenol lyophilized mixture may be packaged in a capsule, emulsion, or tablet such that the *Lactobacillus* are protected in a gastrointestinal tract for transport to an intestine of a subject. In another embodiment, a method for treating Type-1 diabetes including orally administering to a diabetic or pre-diabetic subject, or a subject at risk for becoming pre-diabetic or diabetic, a composition comprising an effective amount of *Lactobacillus*/phenol mixture or lyophilized mixture. In still a further embodiment, of improving immune function in a subject, comprising administering to the subject, the composition comprising an effective amount of *Lactobacillus*/phenol mixture or lyophilized mixture.

4 Claims, 4 Drawing Sheets

(56) References Cited

OTHER PUBLICATIONS

Endo, Akihito et al., "Food matrices and cell conditions influence survival of Lactobacillus rhamnosus GG under heat stresses and during storage", International Journal of Food Microbiology, 2014, vol. 174, pp. 110-112.
Kechagia, Maria et al., "Health Benefits of Probiotics: A Review", ISRN Nutrition, 2013, vol. 2013, Article ID 481651, 7 pages.
Klaenhammer, Todd R. et al., "The impact of probiotics and prebiotics on the immune system", Nature Reviews Immunology, Oct. 2012, vol. 12, pp. 728-734.
Lai, Kin Kwan et al., "Biochemical Properties of Two Cinnamoyl Esterases Purified from a Lactobacillus johnsonii Strain Isolated from Stool Samples of Diabetes-Resistant Rats", Applied and Environmental Microbiology, Aug. 2009, vol. 75, No. 15, pp. 5018-5024.
Leonard, Michael T. et al., "Complete Genome Sequence of Lactobacillus johnsonii Strain N6.2 and Lactobacillus reuteri Strain TD1", Gemome Announcements, May/Jun. 2014, vol. 2, issue 3, e00397-14, 2 pages.
Lorca, G.L. et al., "A Low-pH-lnducible, Stationary-Phase Acid Tolerance Response in Lactobacillus acidophilus CRL 639", Current Microbiology, 2015, vol. 42, pp. 21-25.
Marty-Teysset, C. et al., "Increased Production of Hydrogen Peroxide by *Lactobacillus delbrueckii* subsp. bulgaricus upon Aeration: Involvement of an NADH Oxidase in Oxidative Stress", Applied and Environmental Microbiology, Jan. 2000, vol. 66, No. 1, pp. 262-267.
Nishiyama, Keita et al., "Cell surface-associated aggregation-promoting factor from Lactobacillus gasseri SBT2055 facilitates host colonization and competitive exclusion of Campylobacter jejuni", Molecular Microbiology, 2015, vol. 98 No. 4, pp. 712-726.
Nya, E.J., "Development of Probiotics as Biotechnology-Driven Product for Reducing the Incidence of Gastrointestinal Related Disease", International Journal of Science and Research, Sep. 2015, vol. 4, issue 9, pp. 1748-1751.
Rajam, R. et al., "Microencapsulation of Lactobacillus plantarum MTCC 5422 in fructooligosaccharide and whey protein wall systems and its impacton noodle quality", J Food Sci Technol, Jul. 2015, vol. 52, No. 7, pp. 4029-4041.
Rodrigues, Fabio J. et al., "Effect of natural polymers on the survival of Lactobacillus casei encapsulated in alginate microspheres", Journal of Microencapsulation, Jun. 2017, 11 pages.
Rodriguez-Mateos, Ana et al., "Bioavailability of wild blueberry (poly)phenols at different levels of intake", Journal of Berry Research, 2016, vol. 6, pp. 137-148.
Saarela, Maria et al., "Fibres as carriers for Lactobacillus rhamnosus during freeze-drying and storage in apple juice and chocolate-coated breakfast cereals", International Journal of Food Microbiology, 2006, vol. 112, pp. 171-178.
Sanchez-Rangel, Juan Carlos et al., "The Folin-Ciocalteu assay revisited: improvement of its specificity for total phenolic content determination", Anal.Methods, 2013, vol. 5, 5990-5999.
Shilby, V.K. et al., "Fermented Milks and Milk Products as Functional Food-A Review", Critical Reviews in Food Science and Nutrition, 2013, vol. 53, No. 5, pp. 482-496.
PCT/US2019/0399450, PCT Search Report and Written Opinion, dated Nov. 1, 2019, 9 pages.
Valladares, Ricardo et al., "Lactobacillus johnsonii N6.2 Mitigates the Development of Type 1 Diabetes in BB-DP Rats", PLoS ONE, May 2010, vol. 5, issue 5, e10507, 9 pages.
Valladares, Ricardo et al., "Lactobacillus johnsonii inhibits indoleamine 2,3-dioxygenase and alters tryptophan metabolite levels in BioBreeding rats", Faseb J., 2013, vol. 27, pp. 1711-1720.
Valladares, Ricardo B. et al., "H2O2 production rate in Lactobacillus johnsonii is modulated via the interplay of a heterodimeric flavin oxidoreductase with a soluble 28 Kd PAS domain containing protein", Frontiers in Microbiology, Jul. 2015, vol. 6, article 716, 14 pages.
Van de Guchte, Maarten et al., "Stress responses in lactic acid bacteria", Antonie van Leeuwenhoek, 2002, vol. 82, pp. 187-216.
Wikipedia, "Freeze-drying", Wilkipedia, https://en.wilkipedia.org/w/index.php?title=Freeze-drying&oldid=821904192, Oct. 8, 2019, 8 pages.
Zheng, Xufeng et al., "The mechanisms of the protective effects of reconstituted skim milk during convective droplet drying of lactic acid bacteria", Food Research International, 2015, vol. 76, pp. 478-488.

\* cited by examiner

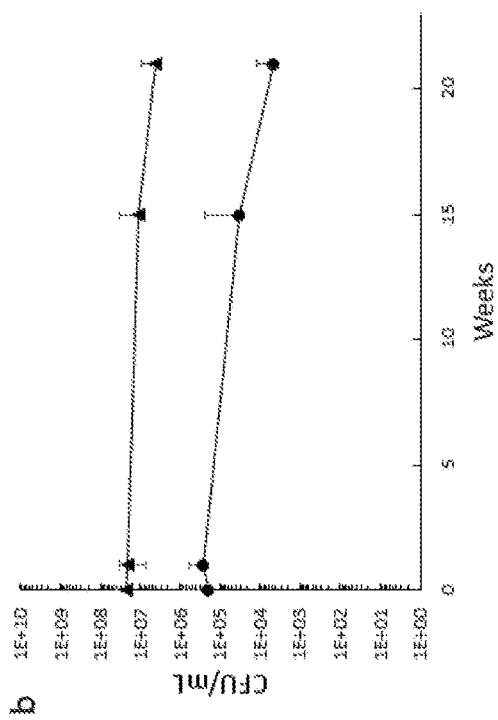
FIG. 2a
FIG. 2b
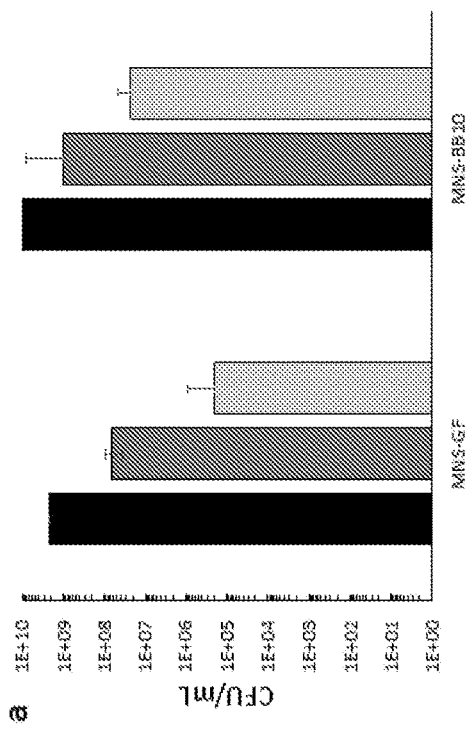
FIG. 2c
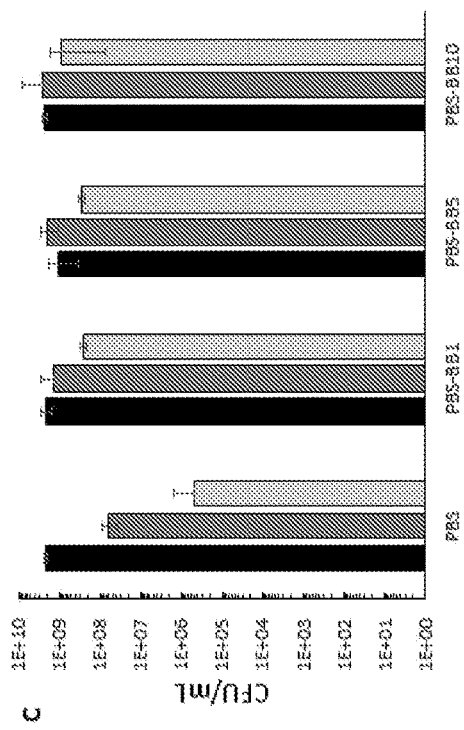
FIG. 2d

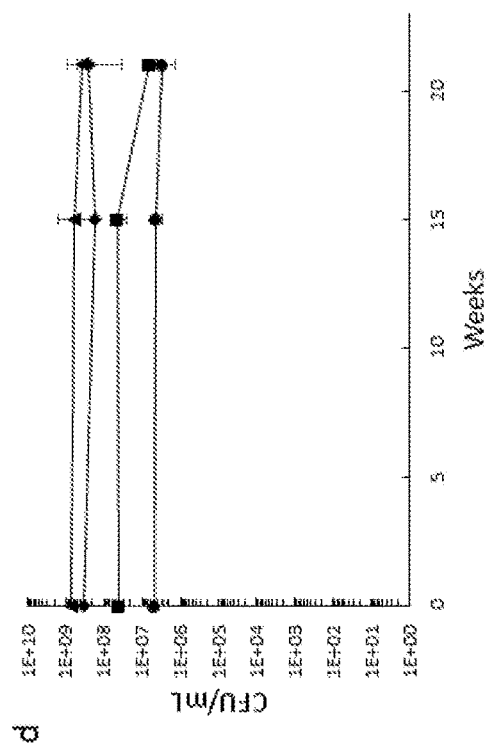
FIG. 4b
FIG. 4d
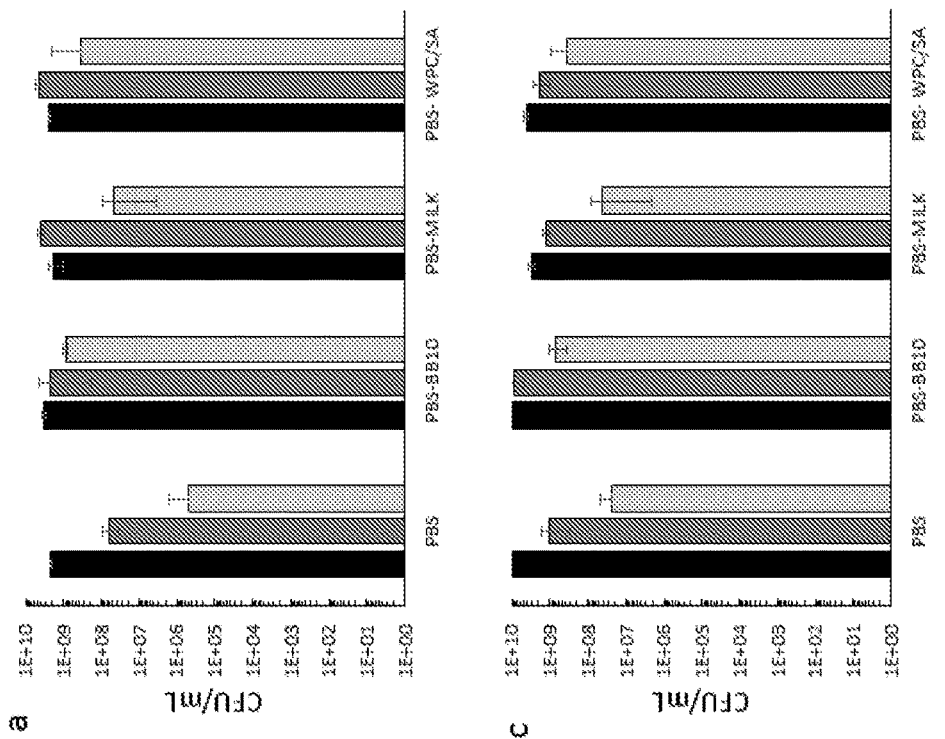
FIG. 4a
FIG. 4c

COMPOSITION OF LACTOBACILLUS AND BERRY EXTRACT

GOVERNMENT SUPPORT STATEMENT

This invention was made with government support under Grant No. 2015-67017-23182 awarded by United States Department of Agriculture. The government has certain rights in the invention.

BACKGROUND

Type 1 diabetes is an autoimmune disease that affects blood sugar regulation. In type-1 diabetes, a person's immune system makes antibodies that destroy the insulin-producing islet beta cells in the pancreas. As a result, the pancreas fails to make insulin. Without insulin, blood sugar increases and cannot be delivered to the muscles and brain where it is needed. Over time, high blood sugar can lead to a number of complications including kidney, nerve, and eye damage, and cardiovascular disease. Moreover, cells do not receive the glucose necessary for energy and normal function. Because people with type 1 diabetes can no longer produce their own insulin, they must inject doses of insulin. They must match the amount of insulin they inject with their diet. Keeping blood sugar in a normal, healthy range (what doctors call "good glycemic control") is the key to preventing long-term deteriorating effects, including as heart disease, diabetic neuropathy, kidney disease, or poor wound healing resulting from high blood glucose levels over a prolonged time period.

BRIEF DESCRIPTION OF DRAWINGS

FIG. 2 a-d. Blueberry aqueous extract increased the resistance of L. johnsonii N6.2 to freeze-drying and improved its survival to storage. (a) Cells were grown for 24 h in MNS-GF or MNS-BB10 under static conditions, washed twice in PBS buffer, resuspended in 1 ml aliquots in PBS and subjected to freeze-drying and (b) stored at 4° C. for 21 weeks: MNS-GF (circle) and MNS-10BB (triangle). (c-d) In addition, cells grown in MNS-GF for 24 h were resuspended in PBS or increasing concentrations of BAE: PBS (circle), PBS-BB1 (diamonds), PBS-BB5 (square) and PBS-BB10 (triangle). The survival of L. johnsonii N6.2 to freeze-drying (c) and during storage of the lyophilized powder at 4° C. (d) was determined. CFU/ml were determined before freezing (black bars), after freezing (dark grey bars) and after freeze-drying (light grey bars). Values shown are the average and standard deviations of experimental triplicates.

FIG. 4 a-d. Blueberry aqueous extract maintains cell viability and functions as a preservative during lyophilization. Cells grown for 24 h in MNS-GF (a-b) or MNS-BB10 (c-d), were resuspended in PBS, PBS-BB10, PBS-milk and PBS-WPC/SA and subjected to freeze-drying. In a and c, survival of L. johnsonii N6.2 was quantified before freezing (black bars), after freezing (dark grey bars) and after freeze-drying (light grey bars). In b and d, survival was determined during storage of the lyophilized powder at 4° C. for 21 weeks: PBS (circle), PBS-BB10 (triangle), PBS-milk (square) and PBS-WPC/SA (diamond). Values shown are the average and standard deviations of experimental triplicates.

DETAILED DESCRIPTION

Figure 1A:
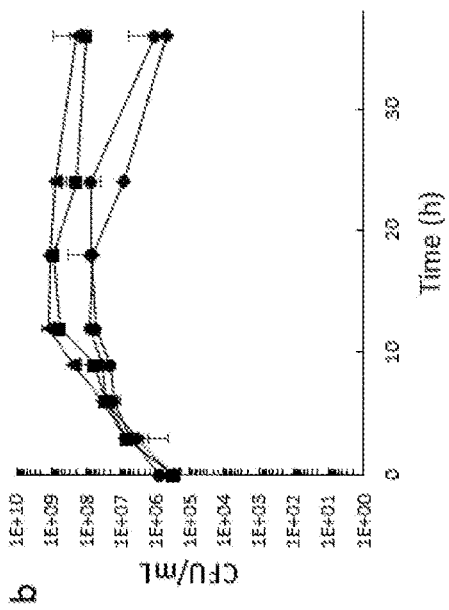
FIG. 1a-c. L. johnsonii N6.2 growth and survival during stationary phase is improved by blueberry aqueous extract under microaerophilic and aerobic conditions. (a) The growth of L. johnsonii N6.2 was assessed under microaerophilic (filled circles) or aerobic conditions (open circles). In the samples collected at different time points (0, 6, 12, 24 and 36 h), the CFU/ml (solid line) and $H_2O_2$ production (dashed line) were determined. (b) The effect of increasing concentrations of BAE was tested by growing L. johnsonii N6.2 in MNS-GF (circles), MNS-BB1 (diamonds), MNS-BB5 (squares) or MNS-BB10 (triangles) under microaerophilic conditions (0 rpm). (c) The effect of the BAE (MNS-BB10) was tested on the growth of L. johnsonii N6.2 under microaerophilic (filled triangles) or aerobic conditions (open triangles). CFU/mL (solid line) and $H_2O_2$ production (dashed line) were determined under these conditions. Values shown are the average and SD of experimental triplicates.

The administration of L. johnsonii has been shown to provide remarkable beneficial effects, particularly in the treatment and prevention of Type 1 diabetes and improving immune functions. See U.S. Pat. No. 9,474,773. Provided herein are new methods of formulating L. johnsonii to increase its bioavailability and effectiveness. It has been discovered that combining a phytophenol compound with L. johnsonii acts not only as a lyophilizing protectant for L. johnsonii, but also acts to increase yield and reduce $H_2O_2$ production in aerobic conditions.

The data provided in the Examples section below relates to testing a phenolic compound containing composition obtained from blueberries. The results indicate that the release of free-phenol compounds from the blueberry extract may have a two-fold benefit on L. johnsonii N6.2 survival by: (i) increasing the radical scavenging activity to decrease the overall oxidative stress and (ii) acting as signaling molecules that may modulate the expression of genes related to the production of $H_2O_2$.

According to one embodiment, a composition is provided comprising a *Lactobacillus* sp. combined with a phenolic compound. In a specific example, the *Lactobacillus* sp. is *L. johnsonii* and the phenolic compound is from an extract of a plant source (i.e. plant extract). The composition may be formulated by methods known to those skilled in the art. In one embodiment, the composition is packaged as a capsule, suppository, tablet, suspension or microemulsion.

Another embodiment pertains to a method of making a composition comprising a *Lactobacillus* sp. The composition comprises admixing *Lactobacillus* sp with a phenolic compound to form a *Lactobacillus*/phenol mixture. The method may further comprise lyophilizing the *Lactobacillus*/phenol mixture to produce a *Lactobacillus*/phenol lyophilized mixture.

Another embodiment pertains to administering the *Lactobacillus*/phenol lyophilized mixture to a subject in need. A subject in need may be a human or non-human mammal in a pre-diabetic or diabetic state or a subject at risk for diabetes (e.g. genetically predisposed to diabetes).

In a further embodiment, composition is administered prior to the onset of clinical manifestation of type 1 diabetes. The time of administration is preferably before extensive irreversible beta cell destruction as evidenced by, for example, the clinical onset of type 1 diabetes. Consequently, in at least one embodiment, treatment is administered to a subject in a pre-diabetic state. In at least another embodiment, treatment is administered to a subject at risk for diabetes. In another embodiment, treatment is administered to a subject in a diabetic state to deter or prevent further damage to the HPB cells in the subject.

In addition, a method is provided wherein the subject exhibits a cytokine-induced pro-inflammatory response, the composition inhibits apoptosis of beta cells.

In yet further embodiments, methods for improving immune function in a subject are provided, including administering to the subject, a *Lactobacillus*/phenol mixture. The method may further include administering the composition to increase expression of Toll like receptor 7 (TLR7) and Toll like receptor 9 (TLR9) in the subject.

Overview

Commensal microorganisms such as *Lactobacillus*, have been used for decades as food supplements due to its probiotic and/or its biotechnological properties (see Kechagia et al. 2013; Klaenhammer et al. 2012; Nya 2015; Shiby and Mishra 2017 for reviews). The Lactobacilli group is described as fastidious-growing due to the large amount of nutrients required for growth. The need of expensive components in media formulations such as amino acids, vitamins and cofactors with contrasting poor biomass yields prevent the possibility of using, at an industrial scale, strains with outstanding probiotic properties. These constraints are furthermore aggravated during the production stage. The starter cultures are exposed to conditions such as heat, freezing, freeze-drying and oxidative stress, diminishing overall cell viability. This is a consequence of bacterial metabolites produced during growth (i.e. $H_2O_2$), mechanical conditions (i.e. shear stress effects) and methods of preservation and storage (i.e. food stabilizing agents). The mechanisms used by *Lactobacillus* species to withstand natural environmental stressors (i.e. lactic acid stress, osmotic and oxidative stress) are quite broad (Bravo-ferrada et al. 2015 Lorca and Valdez 2001). Several studies have indicated that pre-exposure to one of these stresses improves survival to different pressures (van de Guchte et al. 2002). In *L. acidophilus*, the mechanisms triggered to resist the lactic acid stress during the stationary phase of growth resulted in cross tolerance to freeze, lyophilization, and oxidative stress (Lorca and Valdez 2001).

Certainly, these natural adaptive responses to stress are regularly used at industrial level, frequently in combination with the addition of chemical components as preservatives (Endo et al. 2014; Saarela et al. 2006). For example, milk and whey are extensively used as carriers for lyophilization and/or spray-drying (Shiby and Mishra 2017; Zheng et al. 2015). Alternative matrices are currently being explored in probiotics which includes the use of fruit or seeds as carriers during the processing steps (Bhat et al. 2015; Bustamante et al. 2017; Rajam et al. 2015). Many new species/strains of *Lactobacillus* are currently undergoing clinical studies to determine if the probiotic properties identified in vitro/in vivo (cell lines cultures or animal models) are reproducible in human subjects. Optimizing new production and preservation methods for these novel strains is critical to evaluate them towards improving human/animal health. Our laboratory has isolated a new strain of *L. johnsonii* (N6.2) (Lai et al. 2009) that mitigated the onset of diabetes type one in the genetically predisposed BioBreeding animal model (Valladares et al. 2010). Paradoxically, one of the mechanisms involved in modulation of host response is through the production of reactive oxygen species (ROS) (Valladares et al. 2013). We determined that *L. johnsonii* N6.2 is able to produce $H_2O_2$ in the host gastrointestinal system and large amounts when suspended in saline phosphate buffer during the biomass production steps (Valladares et al. 2015). Thus, designing effective methods to produce and preserve *L. johnsonii* N6.2 biomass while maintaining the ability to efficiently generate $H_2O_2$ as a mediator in the host represents an important challenge.

The oxidative stress conditions during industrial manufacturing would represent a large contributor to the survival of *L. johnsonii* N6.2. Based on our analysis, we hypothesized that the addition of a natural compound with antioxidant activity may improve the survival of this strain. In addition, *L. johnsonii* N6.2 has the ability to produce esterases, releasing esterified phytophenols and increasing their redox quenching activity (Lai et al. 2009). In this work, we describe the use of blueberry aqueous extracts (BAE) as a phytophenol source to enhance *L. johnsonii* N6.2 survival during culturing and cell harvesting. Blueberries contain natural compounds with high antioxidant activity due to the high content and diversity of soluble phenolic compounds (Correa-betanzo et al. 2014: Correa-Betanzo et al. 2015).

The results of the Examples disclosed herein demonstrates that *L. johnsonii* N6.2 tolerance to industrial processing stressors such as aeration (oxidative stress), lyophilization (freeze-drying) and shelf-life is improved by utilizing natural antioxidants during production.

Definitions

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

The terms "pre-diabetic," "pre-diabetes," "pre-diabetic state," or "pre type-1 diabetes," as used herein refers to a subject at risk for diabetes, and in particular, a subject at risk for type-1 diabetes. For example, a pre-diabetic patient or subject may have a fasting blood sugar level between 100 and 125 mg/dL.

The term "diabetic state," or "diabetes" as referred to herein refers to a state in which the blood sugar level reaches at least 126 mg/dL, in one example. Symptoms of Type 1 diabetes include frequent urination, excess thirst, weight loss (often sudden), skin infections, bladder/vaginal infections, and abdominal pain. Diabetes may be diagnosed with a blood test, which measures blood sugar level, and also measures levels of insulin and antibodies to confirm the diagnosis.

As used herein, by the term "effective amount," "amount effective," "therapeutically effective amount," or the like, it is meant an amount effective at dosages and for periods of time necessary to achieve the desired result. These terms refers to an amount of an enumerated agent, which, when administered or co-administered in a proper dosing regimen, is sufficient to reduce or ameliorate the severity, duration, or progression of the disorder being treated (e.g., type 1 diabetes), prevent the advancement of the disorder being treated (e.g., type 1 diabetes), cause the regression of the disorder being treated (e.g., type 1 diabetes), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

As used herein, the term "plant extract" refers to a substance derived from a plant source that naturally contains phenolic compounds, including extracts prepared from the whole plant or from various parts of the plant, such as the fruits, leaves, stems, roots, bark, etc. Thus, the method of this invention is not limited to the particular part of the plant used to prepare the extract. The present method can use any source of anthocyanins, proanthocyanidins and/or flavanoids, most typically from botanically derived plant materials such as seeds, fruits, skins, vegetables, nuts, tree barks, and other plant materials that contain phenolic compounds. Most colored fruits, berries, and vegetables are known to contain phenolic compounds. Examples of plants, fruits, berries, and vegetables that contain phenolic compounds include, but are not limited to, blueberries, bilberries, elderberries, plums, blackberries, strawberries, red currants, black currants, cranberries, cherries, raspberries, grapes, currants, hibiscus flowers, bell peppers, beans, peas, red cabbage, purple corn, and violet sweet potatoes. The raw plant material may be used either as is (wet) or may be dried prior to extraction. Optionally, the raw plant material may be presorted by separating and removing the components low in anthocyanins, proanthocyanidins, and/or flavanoids prior to extraction. The plant extract may be an extract in powdered form and reconstituted in an aqueous solution. In a specific example, the extract is blueberry aqueous extract (BAE) comprised of a blueberry powder dissolved in deionized water, centrifuged and filtered.

The term *Lactobacillus* sp. refers to *Lactobacillus johnsonii* and *Lactobacillus reuteri*. In a specific embodiment, *Lactobacillus johnsonii* pertains to a specific strain *L. johnsonii* N6.2. A culture of *Lactobacillus johnsonii* N6.2 has been deposited with the American Type Culture Collection (ATCC), 10801 University Blvd., Manassas, Va. 20110-2209 USA. The deposit has been assigned accession number ATCC No. PTA-122064 by the repository and was deposited on Mar. 19, 2015. The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

As used herein, the terms "phenol(s)" and "phenolic compound(s)" are used interchangeably and include monomeric, oligomeric and polymeric compounds having one or more phenolic groups, and include, but are not limited to, anthocyanins, proanthocyanidins, and flavonoids.

As used herein, the term "phenol-enriched composition" refers to a composition enriched in one or more phenolic compounds and having substantially depleted levels of non-phenolic compounds present in crude extracts of plants, fruits, berries, and vegetables. Examples of such non-phenolic compounds include, but are not limited to, sugars, cellulose, pectin, amino acids, proteins, nucleic acids, plant sterols, fatty acids, and triglycerides. In one embodiment, the phenol-enriched compositions are obtained by obtaining a plant extract from one or more berries and/or fruits containing phenolic compounds including, but not limited to, blueberries, bilberries, elderberries, plums, blackberries, strawberries, red currants, black currants, cranberries, cherries, raspberries, and grapes and subjected the plant extract to a method of separating out the phenolic compounds from non-phenolic compounds.

The compositions disclosed herein may be administered to treat other autoimmune related disorders, including, but not limited to, rheumatoid arthritis, multiple sclerosis, thyroiditis, inflammatory bowel disease, Addison's disease, pancreas transplantation, kidney transplantation, islet transplantation, heart transplantation, lung transplantation, and liver transplantation. The compositions may be administered to improve overall gastric health, i.e., as a probiotic to reduce indigestion, abdominal pain and cephalic syndrome. U.S. Pat. Nos. 9,987,313 and 9,474,773 and PCT Pub. WO2018/112465 disclose various uses for *Lactobacillus johnsonii*, which are incorporated herein by reference. Those skilled in the art would appreciate that the new compositions described herein could be used for above note disorders and in place of the compositions recited in the cited patent references.

The terms "treat", "treating" or "treatment of" as used herein refers to providing any type of medical management to a subject. Treating includes, but is not limited to, administering a composition to a subject using any known method. for purposes such as curing, reversing, alleviating, reducing the severity of, inhibiting the progression of, or reducing the likelihood of a disease, disorder, or condition or one or more symptoms or manifestations of a disease, disorder or condition.

The *Lactobacillus* sp bacteria useful in the disclosed composition may be provided as a live culture, as a dormant material or a combination thereof. Those skilled in the art will appreciate that the *Lactobacillus* sp bacteria may be rendered dormant by, for example, a lyophilization process, as is well known to those skilled in the art.

An example of an appropriate lyophilization process may begin with a media carrying appropriate *Lactobacillus* sp bacteria to which an amount of a phenolic compound may be added for cell protection prior to lyophilization. Examples of phenolic compounds may be provided as an extract from a natural plant source such as a berry (e.g. blueberry). In a further embodiment, an adjunct lyophilization protectant is combined with the *Lactobacillus* sp and phenolic compound prior to lyophilization. Examples of adjunct lyophilization protectants include, but are not limited to, distilled water, polyethylene glycol, sucrose, trehalose, skim milk, xylose, hemicellulose, pectin, amylose, amylopectin, xylan, arabinogalactan, starch (e.g., potato starch or rice starch) and polyvinylpyrrolidone. Gasses useful for the lyophilization process include but are not limited to nitrogen and carbon dioxide.

Compositions

In one aspect, the *Lactobacillus* sp. bacteria in the disclosed composition may be provided as a dispersion in a solution or media. In another aspect, the *Lactobacillus* sp bacteria in the disclosed composition may be provided as a semi-solid or cake. In another aspect, the *Lactobacillus* sp. bacteria in the disclosed composition may be provided in powdered form.

The disclosed compositions may be packaged in pharmaceutically acceptable vehicle, such as capsules, suppositories, tablets, food/drink and the like. Optionally, the disclosed *Lactobacillus*/phenol mixture or lyophilized mixture may include various pharmaceutically acceptable excipients, such as microcrystalline cellulose, mannitol, glucose, defatted milk powder, polyvinylpyrrolidone, starch and combinations thereof.

In one aspect, the disclosed compositions may be prepared as a capsule. The capsule (i.e., the carrier) may be a hollow, generally cylindrical capsule formed from various substances, such as gelatin, cellulose, carbohydrate or the like. The capsule may receive the *Lactobacillus*/phenol mixture or lyophilized mixture therein. Optionally, and in addition to the appropriate *Lactobacillus*/phenol mixture or lyophilized mixture, the capsule may include but is not limited to coloring, flavoring, rice or other starch, glycerin, caramel color and/or titanium dioxide.

In another aspect, the *Lactobacillus*/phenol mixture or lyophilized mixture may be prepared as a suppository. The suppository may include but is not limited to the appropriate *Lactobacillus*/phenol mixture or lyophilized mixture and one or more carriers, such as polyethylene glycol, acacia, acetylated monoglycerides, carnuba wax, cellulose acetate phthalate, corn starch, dibutyl phthalate, docusate sodium, gelatin, glycerin, iron oxides, kaolin, lactose, magnesium stearate, methyl paraben, pharmaceutical glaze, povidone, propyl paraben, sodium benzoate, sorbitan monoleate, sucrose talc, titanium dioxide, white wax and coloring agents.

In a further aspect, the *Lactobacillus*/phenol mixture or lyophilized mixture may be prepared as a tablet. The tablet may include the appropriate *Lactobacillus*/phenol mixture or lyophilized mixture and one or more tableting agents (i.e., carriers), such as dibasic calcium phosphate, stearic acid, croscarmellose, silica, cellulose and cellulose coating. The tablets may be formed using a direct compression process, though those skilled in the art will appreciate that various techniques may be used to form the tablets.

In yet another aspect, the disclosed composition may be formed as food or drink or, alternatively, as an additive to food or drink, wherein an appropriate quantity of *Lactobacillus*/phenol mixture or lyophilized mixture is added to the food or drink to render the food or drink the carrier.

The concentration of the *Lactobacillus* sp. bacteria in the disclosed composition may vary depending upon the desired result, the type of bacteria used, the form and method of administration, among other things. For example, a composition may be prepared having a count of *Lactobacillus* sp. bacteria in the preparation of no less than about $1 \times 10^6$ colony forming units per gram, based upon the total weight of the preparation.

Alternatively, one or more other excipients may be included in the composition to (1) impart satisfactory processing and compression characteristics to the composition (e.g., adjust the flowability, cohesion and other characteristics of the composition) and (2) give additional desirable physical characteristics to the tables (e.g. color, stability, hardness, disintegration). Mostly the excipients aid in the delayed release of the drug from the composition to achieve regional delivery to the lower GI. As used herein, the term "excipient" may include all excipients present in the dosage form, including all components other than the drug entity and the hydrocolloid gum from higher plants. A plurality of excipient substances may be present in any dosage form, and may include multiple substances having similar pharmaceutical function (e.g., lubricants, binders, diluents) or similar structure (e.g., a mixture of monosaccharides). Preferably the fewer excipients present the better. Such excipients are present in an amount sufficient to provide the composition with the desired delayed release/regional delivery characteristics, hardness rating and handling characteristics and will generally be present at a level of about 2% by weight to about 50% by weight, preferably about 2% by weight to about 40% by weight and more preferably about 2% to about 10% by weight. Excipients may be selected from many categories known in the pharmaceutical arts. The excipients used will be chosen to achieve the desired object of the invention keeping in mind the activity of the drug being used, as well as its physical and chemical characteristics such as water solubility and possible interactions with the excipients to be used.

For example with drugs that are more water soluble, generally a lower percentage by weight of excipients will be used, i.e., less than about 20% or from about 2% to about 15% by weight, preferably no more than about 10% by wt, while for drugs that are less water soluble a higher percentage by weight may be used, e.g., about 20% up to about 40% by wt. These levels may be adjusted to achieve the desired hardness and porosity of the final tablet composition to obtain the delayed release profile.

From the foregoing discussion, it is seen that one aspect of this invention is a particle mass of a solid dosage form that can be administered orally as a tablet. Thus, the composition is neither a liquid nor a gas, but a solid tablet having an amount of drug as a unit dosage. Generally, this unit dosage will be an amount that can be swallowed by a human subject and may vary from a total of about 100 milligrams to about 1500 mg, preferably no more than about 1200 mg and particularly no more than about 800 mg. For children, the size of the tablet may be significantly less than for adults, and for elderly patients who have difficulty swallowing, the total amount may be less than what would be viewed as a normal amount for adults. It is to be understood that the tablets of this invention may be designed as a single tablet having a unit dosage amount or several smaller tablets, e.g. 2-5, may be combined in a capsule for oral administration. The composition used to prepare the tablet may be granulated.

In a typical embodiment, the composition is formulated in accordance with routine procedures as a pharmaceutical composition adapted for oral administration to humans.

The amount of the *Lactobacillus* sp. which will be effective in the treatment of a particular disease or disorder will depend on the nature of the disease or disorder, and can be determined by standard clinical techniques. In addition, in vitro and in vivo assays may optionally be employed to help identify optimal dosage ranges. The dosage will depend on the body weight of the subject. However, in one example suitable dosage ranges for oral administration or parenteral administration may be about 10 pg to 100 mg, 20 pg to 50 mg, 0.1 mg to 20 mg, or 0.5 mg to 10 mg (calculated either per kg body weight or as total dose per individual). Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain an active ingredient in the range of 0.5% to 10% by weight; oral formulations preferably contain 10% to 95% active ingredient.

The general approaches to delivering drugs to the lower GI tract (e.g. small intestine and colon) for interaction with immune cells in the mucosa of the lower GI tract include: 1) enteric coating designed to release drug in the more alkaline environment of the gastrointestinal tract, 2) bioerodible coatings and matrices, 3) prodrugs, 4) timed-release systems and, 5) enteric polymeric material-based release systems that release drug after they transit through the stomach and reach the intestines. A general discussion of these approaches and others may be found in PCT Patent application No. PCT/US91/03014 by Sintov and Rubinstein.

Process of Preparation

Capsules containing *Lactobacillus* sp. can be prepared according to known techniques. See for example US Pat. Pub. 20170368049 incorporated by reference. For preparing solid compositions such as tablets, the principal active ingredient may be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the intestine or lower GI tract, or to otherwise be delayed in release. A variety of materials can be used for such enteric layers or coatings, such materials including a number of polymeric acids and mixtures of polymeric acids with such materials as shellac, acetyl alcohol and cellulose acetate.

In preparing the tablet compositions of this invention one may use pharmaceutical compression or molding techniques, preferably the former due to its adaptability to large scale production methods. Using techniques known in the art, the tablets of the invention may take any appropriate shape such as discoid, round, oval, oblong, cylindrical, triangular, hexagonal, and the like. The tablets may be coated or uncoated. If coated they may be sugar-coated (to cover objectionable tastes or odors and to protect against oxidation), film coated (a thin film of water soluble matter for similar purposes), or enteric coated (to resist dissolution in gastric fluid but allow disintegration of the coating in the small intestine—as discussed herein before). Depending on whether the tablet is a uniform matrix tablet, an active core tablet or a concentration gradient tablet, the process for preparation will vary slightly.

In order to ensure tablet hardness and uniformity of weight, content and other items, it is preferable to prepare the tablets having the composition of this invention by using a pre-granulation technique. In general, the granulation techniques can include the wet granulation method, the fluid bed granulation method, the dry granulation method or direct compression.

Once the tablets are appropriately formed, they can then be coated by any of the necessary coating techniques as discussed in Chapter 90 of Remington's. For example, the tablets may be sugar-coated in accordance with the procedure discussed therein or film coated or preferably enterically coated. Enteric coating is preferred in the tablets of this invention to minimize the release of any of the drug in the upper GI and assure the release to the lower GI particularly the colon. As much as pertinent of the Remington's sections of Chapters 88 and 90 is incorporated herein by reference.

Administration

In some embodiments, the composition embodiments comprising *Lactobacillus* sp. described herein will be administered orally to a mammalian subject in need thereof using a level of pharmaceutical composition that is sufficient to provide the desired physiological effect. The mammalian subject may be a domestic animal or pet but preferably is a human subject. The level of pharmaceutical composition needed to give the desired physiological result is readily determined by one of ordinary skill in the art. Other parameters that may be taken into account in determining dosage for the pharmaceutical composition embodiments described herein may include disease state of the subject or age of the subject.

The compositions may take the form of suspensions, solutions or emulsions in oily or aqueous vehicles and may contain formulatory agents such as suspending, stabilizing and/or dispersing agents. In some embodiments, the composition embodiments described herein may be administered orally or intravenously via parenteral nutritional therapy to a subject via an emulsion. The emulsion may include, in some embodiments, an aqueous continuous phase and a dispersed phase. The boundary between the phases called the "interface". The present emulsions are adapted for application to a mucosal surface of a vertebrate animal, preferably a mammal, including humans. These compositions improve the permeability and bioavailability of active compounds after application to a mucous surface. Mucosal surfaces of interest include the intestinal mucosa. Use of bioadhesive polymers in pharmaceutical emulsions affords enhanced delivery of drugs in bioadhesive polymer-coated suspensions, in some examples. Bioadhesive pharmaceutical emulsions may be used to deliver the *Lactobacillus* sp. described herein to: a) prolong the residence time in situ, thereby decreasing the number of drug administrations required per day; and b) may be localized in the specified region to improve and enhance targeting and bioavailability of delivered drugs.

The ability to retain and localize a drug delivery emulsion in a selected region leads to improved bioavailability, especially for drugs exhibiting a narrow window of adsorption due to rapid metabolic turnover or quick excretion. Intimate contact with the target absorption membrane improves both the extent and rate of drug absorption.

Bioadhesion is the characteristic of certain natural and synthetic polymers of binding to various biological tissues. Of particular interest are polymers which bind to the mucous lining that covers the surface of many tissues which communicate directly or indirectly with the external environment, such as the gut, for example. Mucus binding polymers may be referred to as mucoadhesive. Several bioadhesive, and specifically mucoadhesive, polymers are known. The chemical properties of the main mucoadhesive polymers are summarized as follows:

a. strong H-bonding groups (—OH, —COOH) in relatively high concentration;

b. strong anionic charges;

c. sufficient flexibility of polymer backbone to penetrate the mucus network or tissue crevices;

d. surface tension characteristics suitable for wetting mucus and mucosal tissue surfaces; and e. high molecular weight.

Bioadhesive polymers may be used in the pharmaceutical composition embodiments described herein, examples of bioadhesive polymers currently used in pharmaceutical preparations include: carboxymethylcellulose (CMC), hydroxypropylmethylcellulose (HPMC), polyacrylic and polymethacrylic acid and their derivatives, pectin, alginic acid, chitosan, polyvinylpyrrolidone, hyaluronic acid, and polyvinyl alcohol. The most frequently used polymer is Carbopol (Carbomer), which is a high molecular weight polyacrylic acid polymer. It is used in many formulations for bioadhesive drug delivery systems, as a suspending agent, as a tablet coating, and in ocular suspensions.

Pharmaceutical composition embodiments described herein may include the composition comprising a *Lactobacillus*/phenol lyophilized mixture. incorporated into inert lipid carriers such as oils, surfactant dispersions, emulsions, liposomes etc. Self-emulsifying formulations are ideally isotropic mixtures of oils, surfactants and co-solvents that emulsify to form fine oil in water emulsions when introduced in aqueous media. Fine oil droplets would pass rapidly from stomach and promote wide distribution of drug throughout the GI tract, thereby overcome the slow dissolution step typically observed with solid dosage forms. These embodiments may provide control release self-emulsifying pellets, microspheres, tablets, capsules etc. that increase the use of "self-emulsification.".

In further embodiments, *Lactobacillus*/phenol lyophilized mixture composition embodiments described herein may be microencapsulated for delivery to a subject. Microencapsulation (ME) offers the potential to reduce the adverse effects on probiotic viability in the gastrointestinal (GI) tract environment. ME separates microorganism cells from their environment until they are released. Controlled release of the *Lactobacillus* is a particular benefit of ME. It is beneficial for encapsulated probiotic microorganisms to be released in the small intestine where the Peyer's patches exist to activate the immune system, in some embodiments.

Oral delivery will be the most straightforward mode of administration to deliver the *Lactobacillus* sp. to the gut mucosa. However, in alternative embodiments, other methods of administration are contemplated. Accordingly, suitable methods for administering a *Lactobacillus* sp. containing composition (e.g., *Lactobacillus*/phenol lyophilized mixture) in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered orally, intravenously, intranasally, or intraperitoneally to thereby treat a disease or disorder.

Regardless of the route of administration, the compositions of the presently-disclosed subject matter typically not only include an effective amount of a *Lactobacillus* sp. but are typically administered in amount effective to achieve the desired response. As such, the term "effective amount" is used herein to refer to an amount of the therapeutic composition (e.g., a *Lactobacillus* sp., and a pharmaceutically vehicle, carrier, or excipient) sufficient to produce a measurable biological response (e.g., a decrease in diabetes symptoms or increase in immune function). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Examples

*L. johnsonii* N6.2 Growth Conditions

*L. johnsonii* N6.2 was routinely grown in MRS broth (Remel, Lenexa, Kans., USA). MNS media is a modified MRS broth without glucose, formulated as follows: peptone 10 g, meat extract powder 10 g, yeast peptone 5 g, $K_2HPO_4$ 2 g, sodium acetate 5 g, ammonium citrate tribasic 2 g, $MgSO_4.7H_2O$ 0.2 g, $MnSO_4.H_2O$ 0.05 g, and Tween-80 1 g raised to a final volume of 1 L with distilled water, pH=6.5±0.2. To prepare blueberry enriched media (MNS-BB), the blueberry powder (Tifblue/Rubel 50/50 blend, US Highbush Blueberry Council, Folsom, Calif., USA), was dissolved in deionized water (at 1, 5 or 10% w/v), stirred for 60 min, and then centrifuged at 12000 rpm for 30 min at 4° C. The pellet was discarded and the supernatant filtered (Whatman No. 1 filter paper). The resulting BAE was used to solubilize the components of the MNS media. The resulting solubilizations constitute MNS-BB1, MNS-BB5, and MNS-BB10 in accordance with the different blueberry concentrations. MNS-GF is MNS media supplemented with 3% w/v of glucose and 3% w/v of fructose. All culture media were sterilized by filtration (0.22 µm).

To prepare the inoculum, *L. johnsonii* N6.2 culture grown for 16 h at 37° C. without agitation was inoculated at an initial OD=0.05. When aerobic conditions were used, the cultures were incubated in a shaker at 100 rpm at 37° C. Cell growth was monitored by periodic measurements of the culture's optical density at 600 nm ($OD_{600}$). Colony forming units (CFU/ml) were determined by performing serial dilutions with peptone water (peptone extract 0.9% w/v). Subsequently, the cell suspensions were plated on MRS agar plates. Plates were incubated at 37° C. for 48 h under microaerophilic conditions.

Determination of $H_2O_2$

The production of $H_2O_2$ was determined by using colorimetric strips following the manufacturer's instructions (Quantofix, Macherey-Nagel, Germany). Alternatively, Amplex, Red Hydrogen peroxide/peroxidase assay kit (Invitrogen, CA, USA) and 4-aminoantipyrine and phenol (AAP) were used (Marty-Teysset et al. 2000).

Phytophenol Processing and Recovery

Residual phenolic in growth media (MNS-GF or MNS-BB10) were recovered as follows: samples of the growth media were taken at different time points along *L. johnsonii* N6.2 growth kinetics. The supernatant was recovered by centrifugation (4000 g for 30 min at 4° C.) and saved as aliquots at −20° C. until processing. Soluble phenolic compounds were recovered by solid-phase extraction using a C18 HYPERSEP column (ThermoScientific, WI, USA) as described by Correa-Betanz et al. (2015).

Determination of Total Polyphenols

The total polyphenol content in MNS-GF or MNS-BB10, as well as in the purified fractions were quantified using Folin-Ciocalteau's reagent according to Sànchez-Rangel et al. (2013) with slight modifications. Briefly, the samples (15 µL) were diluted in 240 µL of distilled water in a 96-well microplate. Then, 15 µL of the Folin-Ciocalteau's phenol reagent, 2N (Sigma-Aldrich, USA) was added and the mixtures were incubated 5 min at room temperature. The characteristic blue color was developed by adding 30 µL of 5% $Na_2CO_3$ solution. The plates were incubated in the dark for 2 h at room temperature before measuring the absorbance. The absorbance of the samples was measured at 725 nm using a Sinergy HT microplate reader (Biotek, Winooski, Vt., USA). The total phenolic concentration was estimated from a calibration curve using gallic acid as standard control. The polyphenol concentration was expressed as micrograms (µg) of gallic acid equivalent per mL of sample.

Radical Scavenging Activity

The total scavenging activity of the culture media was assessed by using the DPPH method described by Dong et al. (2017). The samples (MNS-GF, MNS-BB10 or its polyphenol enriched fractions) were diluted (½ and ¹⁄₁₀) in methanol. The reaction mixture containing 20 µL of each sample and 180 µL of 0.2 mM DPPH solution was incubated at room temperature for 30 min. The quenching ability of L-ascorbic acid was used as a positive control. The absorbance was measured at 515 nm using a Sinergy HT microplate reader (Biotek, Winooski, Vt., USA). The scavenging activity (SA) was estimated by the following formula: % $SA=[(Abs_{control-blank}-Abs_{sample-blank})/Abs_{control-blank}]\times 100$. Total radical scavenging activity (% SA) is expressed in percent of quenching activity per µg of gallic acid equivalents.

Evaluation of Aqueous Blueberry Extract on the Survival of *L. johnsonii* N6.2 to Freeze-Drying The effect of different cryo/drying preservatives was tested on the tolerance of *L. johnsonii* N6.2 to freeze-drying. *L. johnsonii* N6.2 was grown in MNS-GF or MNS-BB10 media to stationary phase (24 h of growth), centrifuged (6000 rpm for 20 min at 4° C.) and the pellet obtained was washed once with phosphate-buffered saline (PBS pH=7.4). The bacteria were resuspended as a 10× concentrate in PBS with skim milk (10% w/v), whey protein concentrate and sodium alginate (WPC/SA, 20% and 1% w/v respectively) or PBS-BB buffer (PBS supplemented with 1, 5 or 10% blueberry powder, solubilized and filtered as indicated above). Bacteria cells suspended in PBS were used as controls. Frozen samples maintained at −80° C. for 24 h were lyophilized and the freeze-dried powder was stored at 4° C. to evaluate further cell viability.

Results

*L. johnsonii* N6.2 Shows Reduced Survival During Stationary Phase of Growth.

*L. johnsonii* N6.2 growth and survival were evaluated by cell counts and expressed as CFU/ml of culture media (FIG. 1). The cultures were incubated with agitation (aerobic) and static (microaerophilic) conditions to compare aeration effects on cell growth and viability. Both growth conditions resulted in similar growth kinetics during the first 12 h of growth ($OD_{600}>1.0$). However, growth in aerobic cultures halted thereafter showing a drastic drop in cell viability as was demonstrated by CFU counts (FIG. 1a). After 36 h of growth, this culture showed a total decrease of 5-log units. The loss of cell viability correlated with a large accumulation of $H_2O_2$ measured in the culture media (880 µM of $H_2O_2$) (FIG. 1a).

In contrast, microaerophilic cultures showed that cell viability decreased only by 1-log unit after 24 h of growth. The amount of $H_2O_2$ at 36 h of growth did not increase beyond 88 µM. No significant differences were observed in pH when comparing both cultures. These results suggest that *L. johnsonii* N6.2 growth and viability in MRS media is strongly affected by oxidative stress in the form of $H_2O_2$ rather than its production of organic acids. In addition, this data supports our previous findings where *L. johnsonii* N6.2 is able to produce $H_2O_2$ when cells are aerobically suspended in PBS (Valladares et al. 2015).

Blueberry Aqueous Extract Improved *L. johnsonii* N6.2 Growth and Survival to Aerobic Stress.

The previous results prompted us to evaluate bacterial growth in a media supplemented with antioxidants. Since blueberries have a high phytophenol content with high antioxidant potential (Correa-betanzo et al. 2014), the effect of total blueberry extract was tested on *L. johnsonii* N6.2 growth. The blueberry powder utilized in this study contains 600 g/kg of total metabolizable sugars. The main carbohydrates, glucose and fructose, are presented in a 1:1 relationship. To perform the assays at a comparable concentration of sugars used in the standard MRS culture media, a new culture media without glucose was formulated (MNS). The MNS media was amended with increasing concentrations (1, 5 or 10% w/v) of freeze-dried BB to reach a final sugar content of 6, 30 and 60 g/L, named MNS-BB1, MNS-BB5 and MNS-BB10, respectively. The culture media used as a control (MNS-GF) was formulated by adding glucose and fructose in a 1:1 relationship in order for it to be comparable to the total metabolizable sugars found in the blueberry powder.

Figure 1B:
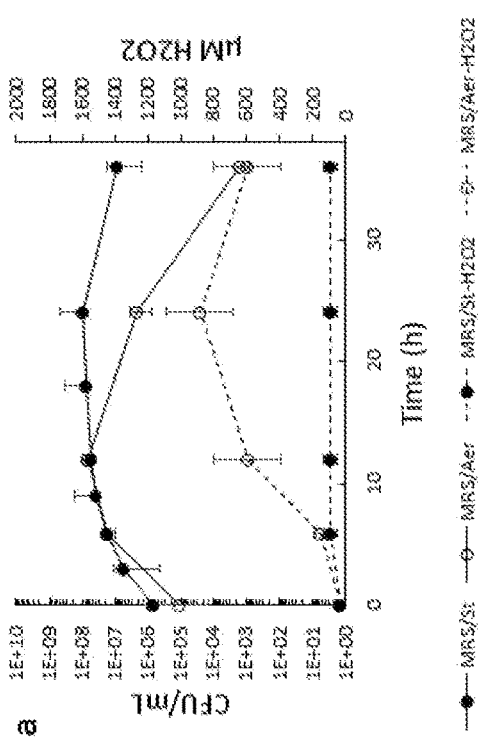
Figure 1C:
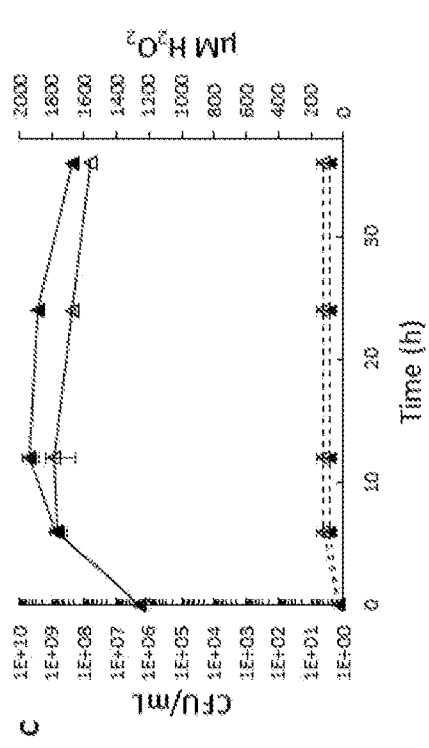

The first assay performed was to evaluate the effects of BAE on *L. johnsonii* N6.2 growth and cell survival in a microaerophilic environment. In the control media, MNS-GF, *L. johnsonii* N6.2 reached $5 \times 10^7$ CFU/ml after 12 h of growth (FIG. 1b). These cells maintained full viability during the first 24 h of growth, but decreased to $1 \times 10^6$ CFU/ml after 36 h of growth. The cultures formulated with 1% BAE did not inhibit growth, but rather the observed growth rates were comparable to that obtained in MNS-GF. Interestingly, after 12 h of incubation the media formulated with 5 and 10% BAE reached $1 \times 10^9$ CFU/ml. When cells were challenged to grow aerobically in MNS-BB10 (100 rpm), the highest cell count of $1 \times 10^9$ was obtained after only 8 h of growth (FIG. 1c). This represents a significant improvement in biomass productivity when compared to MRS. In addition, cell viability decreased only 1-log after 36 h of growth and more importantly, the $H_2O_2$ remained lower than 80 µM (detection limit) under these conditions (FIG. 1c).

In the supernatants collected from this assay, polyphenols, soluble low molecular weight phenolic compounds, and total scavenging activity of the culture media were measured. Both aerobic and anaerobic conditions were compared and the results are summarized in Table 1. The total phenolic compounds (polyphenols+soluble free phenols) remained almost constant during the first 12 h of growth with slight decrease after 24 h of growth. However, no significant differences were observed between both conditions. Since reducing sugars, such as those found in blueberry, are able to interfere with the Folin-Ciocalteu method in determining total phenolic content, the phenolics were purified from the fermented media and quantified. Interestingly, we observed a steady increase in the purified phenolics isolated from the culture media in both conditions in a growth dependent manner, where the free phenolics were double the concentration determined at the beginning of the assay (See Table 1). The increase in free phenol fractions over time reflects the ability of *L. johnsonii* N6.2 to release esterified phenolics present in the BAE, potentially, due to the enzyme activity of its cinnamoyl esterases.

The total antioxidant activity was determined using the DPPH radical scavenging (% SA) method. Scavenging activity (% SA) is expressed as reducing equivalents of 1 µg of gallic acid (GAE) determined from the phenolic content of each sample. No significant differences were observed comparing the growth conditions when the total polyphenol fraction was analyzed. However, significant changes were observed in the purified free phenol fraction over time (Table 1). The increase in % SA was independent of the growth condition. It was found that the quenching activity increased from % SA=68.4±10.3 to % SA=96.3±5.9 after 36 h of microaerophilic growth conditions. Similar values were obtained for the aerobic cultures (% SA=72.3±3.6 to % SA=99.3±2.5). This reducing power is equivalent to 2-3 µg of L-ascorbic acid (% SA=20.2±0.85). The results suggest that the increasing quenching ability of the culture media is a direct consequence of the cinnamoyl esterase of *L. johnsonii* N6.2 previously described (Lai et al. 2009).

The Addition of Blueberry Aqueous Extract to the Growth Media Improved *L. johnsonii* N6.2 Survival to Freeze Drying.

The tolerance of *L. johnsonii* N6.2 to freeze-drying stress during lyophilization was evaluated comparing cells cultured in MNS-GF and MNS-BB10. *L. johnsonii* N6.2 was grown in each media for 24 h under static condition, washed, resuspended in PBS, frozen, and then subjected to freeze-drying. No additional preservatives were used at this step. Viable cell counts were determined at each step of the procedure: namely before freezing at −80° C., after freezing at −80° C. for 24 h and immediately after the freeze-drying step. The cells grown in MNS-GF and in MNS-BB10 showed a similar tolerance to freezing stress (a decrease in 1.5- and 1-log in CFU/ml, respectively) while the cells grown in MNS-GF were significantly more sensitive to the drying step, decreasing 2.5-log units (FIG. 2a). Meanwhile, cells grown in MNS-BB10 showed a decrease of only 1.4-log units (FIG. 2a). Aliquots of the freeze-dried samples were maintained for 21 weeks at 4° C. These samples were used to evaluate the viability of freeze-dried cells after rehydration. The results obtained suggest that cells grown in MNS-GF were less viable (decreased 2-log units) than the cells collected from MNS-BB10 cultures that only decreased in 1-log unit from Week 0 (FIG. 2b). In summary, in absence of additional preservatives during freeze-drying, cells grown in MNS-BB10 showed increased resistance to the lyophilization/storage process (a combined reduction in 3.5-log) when compared to MNS-GF cultures where we observed a reduction of 6.0-log units when comparing to pre-freezing bacterial counts.

Blueberry Aqueous Extract is an Effective Protectant for Lyophilization.

Our next goal was to determine whether or not the addition of BAE to PBS solution used to suspend the cells prior to the freeze-drying step would increase the survival of *L. johnsonii* N6.2. Cultures grown in MNS-GF for 24 h were washed and suspended in PBS containing increasing concentrations of BAE to final concentrations of 1, 5 or 10% w/v (PBS-BB1, PBS-BB5 and PBS-BB10, respectively) (FIGS. 2c and d). It was observed that the survival of *L. johnsonii* N6.2 after freeze-drying improved with increasing concentrations of BAE (FIG. 2c). A 100% survival to freezing was observed in all conditions containing blueberry (PBS-BB1, PBS-BB5 or PBS-BB10). Interestingly, even the lowest concentration of BAE was able to improve the survival to the freeze-drying process. The cells preserved in PBS showed a drastic decrease in viability, dropping 2.5 log units from the freezing to freeze-drying step (FIG. 2c). In contrast, the survival to storage at 4° C. was highly affected by the concentration of BAE. A steady decrease in survival was observed for cells lyophilized in either PBS or PBS-BB1, while cells in PBS-BB5 or PBS-BB10 resulted in a close to 100% survival for up to 21 weeks (FIG. 2d).

Figure 3B:
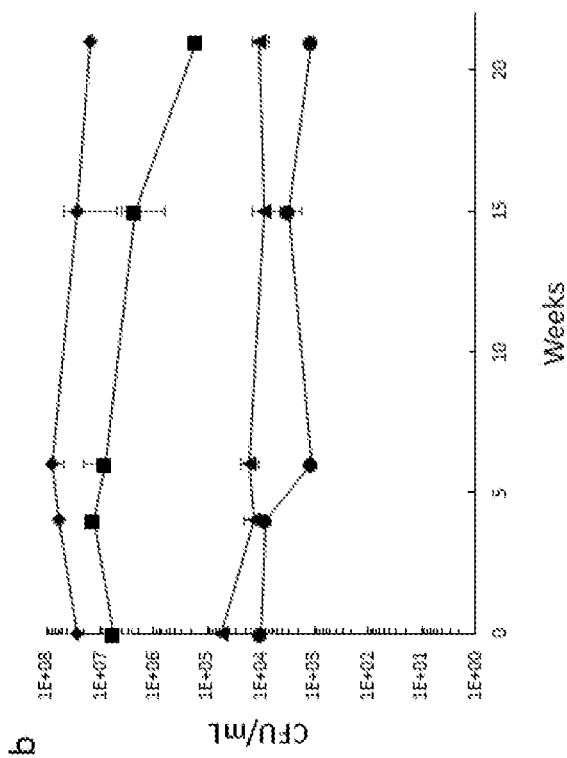
FIG. 3 a-b. The addition of blueberry aqueous extract to L. johnsonii N6.2 cells grown under aerobic conditions increase the resistance to freeze-drying and improved its survival to storage. (a-b) Cells were grown for 24 h in MNS-GF or MNS-BB10 under aerobic conditions, washed twice in PBS buffer, resuspended in either 1 ml aliquots in PBS or PBS-BB10, as indicated on the bottom of the figure. (a) Cells were subjected to freeze-drying and the survival of L. johnsonii N6.2 was quantified before freezing (black bars), after freezing (dark grey bars) and after freeze-drying (light grey bars). In b, survival was determined during storage of the lyophilized powder at 4° C. for 21 weeks: MNS-GF/PBS (circle), MNS-BB10/PBS (square), MNS-GF/PBS-BB10 (triangle) and MNS-BB10/PBS-BB10 (diamond). Values shown are the average and standard deviations of experimental triplicates.
Figure 3A:
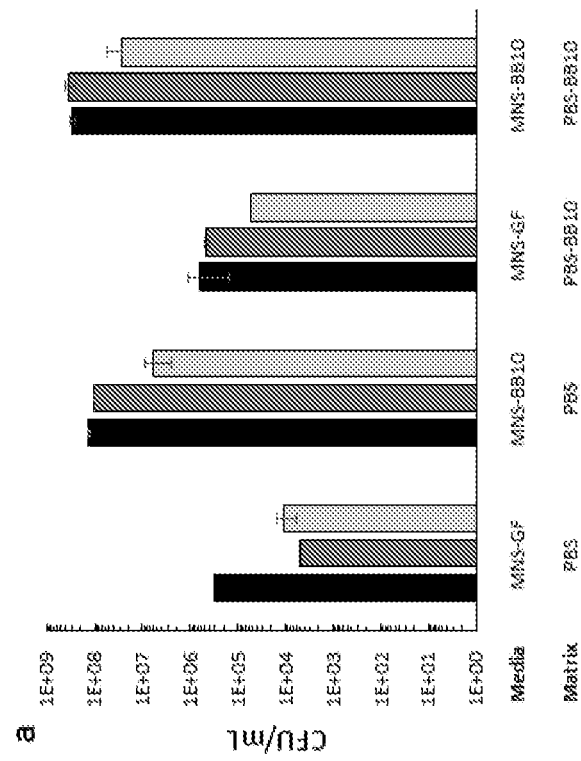

The effect of BAE was determined on *L. johnsonii* cultures grown under aerobic conditions (FIG. 3). Similarly to the cells grown under static conditions, the combined use of BAE as a media supplement (MNS-BB10) or as a preservative (PBS-BB10) provided the maximal tolerance to lyophilization and subsequent storage at 4° C. (FIG. 3).

Blueberry as a Culture Additive Improves the Activity of Commonly Used Cryoprotectants.

Next, we analyzed the combined effect of BAE when it was added to the growth media and when used as an additive during lyophilization. Cells were grown to stationary phase in either MNS-GF (FIGS. 4a and b) or MNS-BB10 (FIGS. 4c and d) and then lyophilized in the absence (PBS) or presence of BAE (PBS-BB10). It was found that the use of BAE in both the growth media and as an additive resulted in maximal survival to freeze-drying (FIGS. 4a and c).

The protective effect of the BAE was compared to other commonly used protectants during lyophilization such as 10% skim milk (PBS-milk) or microencapsulation using whey protein-sodium alginate (PBS-WPC/SA). It was found that PBS-milk and PBS-WPC/SA resulted in an almost 100% survival after freezing cells grown in either MNS-GF (FIG. 4a) or MNS-BB10 (FIG. 4c). For cells grown on MNS-GF, a significant difference (p<0.039) was observed after the drying step among the preservatives used, these being PBS-BB10>PBS-WPC/SA>PBS-milk (FIG. 4a). A similar trend was observed in *L. johnsonii* N6.2 grown in MNS-BB10 where the survival in PBS-Milk was slightly below the results obtained by MNS-BB10 and PBS-WPC/SA (FIG. 4c). In all cases, the BAE demonstrated to be a superior protectant to storage (FIGS. 4b and d). In the case of microencapsulated cells, the preservation was comparable only when the cells were grown in presence of BAE (FIG. 4d).

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

REFERENCES

Bhat, R., Suryanarayana, L. C., Chandrashekara, K. A., Krishnan, P., Kush, A., & Ravikumar, P. (2015). *Lactobacillus plantarum* mediated fermentation of *Psidium guajava* L. fruit extract. *Journal of Bioscience and Bioengineering*, 119(4), 430-432. https://doi.org/10.1016/j.jbiosc.2014.09.007

Bravo-ferrada, M., Brizuela, N., & Gerbino, E. (2015). Effect of protective agents and previous acclimation on ethanol resistance of frozen and freeze-dried *Lactobacillus plantarum* strains. Cryobiology 71, 522-528. https://doi.org/10.1016/j.cryobiol.2015.10.154

Bustamante, M., Oomah, B. D., Rubilar, M., & Shene, C. (2017). Effective *Lactobacillus plantarum* and *Bifidobacterium infantis* encapsulation with chia seed (*Salvia hispanica* L.) and flaxseed (*Linum usitatissimum* L.) mucilage and soluble protein by spray drying. *Food Chemistry*, 216, 97-105. https://doi.org/10.1016/j.foodchem.2016.08.019

Correa-betanzo, J., Allen-vercoe, E., Mcdonald, J., Schroeter, K., Corredig, M., & Paliyath, G. (2014). Stability and biological activity of wild blueberry (*Vaccinium angustifolium*) polyphenols during simulated in vitro gastrointestinal digestion. *FOOD CHEMISTRY*, 165, 522-531. https://doi.org/10.1016/j.foodchem.2014.05.135

Correa-Betanzo, J., Padmanabhan, P., Corredig, M., Subramanian, J., & Paliyath, G. (2015). Complex formation of blueberry (*Vaccinium angustifolium*) anthocyanins during freeze-drying and its influence on their biological activity. *Journal of Agricultural and Food Chemistry*, 63(11), 2935-46. https://doi.org/10.1021/acs.jafc.5b00016

Costa, M. G., Ooki, G. N., Vieira, A. D., Bedani, R., & Saad, S. M. (2017). Synbiotic Amazonian palm berry (açai, *Euterpe oleracea* Mart.) ice cream improved *Lactobacillus rhamnosus* GG survival to simulated gastrointestinal stress. *Food & Function*, 8(2): 731-740. doi: 10.1039/c6fo00778c.

Dong, L.-M., Jia, X.-C., Luo, Q.-W., Zhang, Q., Luo, B., Liu, W.-B., . . . Tan, J.-W. (2017). Phenolics from *Mikania micrantha* and Their Antioxidant Activity. *Molecules* (Basel, Switzerland), 22(7). https://doi.org/10.3390/molecules22071140

Endo, A., Teräsjärvi, J., & Salminen, S. (2014). Food matrices and cell conditions influence survival of *Lactobacillus rhamnosus* GG under heat stresses and during storage. *International Journal of Food Microbiology*, 174, 110-2. https://doi.org/10.1016/j.ijfoodmicro.2014.01.006

Kechagia, M., Basoulis, D., Konstantopoulou, S., Dimitriadi, D., Gyftopoulou, K., Skarmoutsou, N., & Fakiri, E. M. (2013). Health Benefits of Probiotics: A Review. *ISRN Nutrition*, 2013, 1-7. https://doi.org/10.5402/2013/481651

Klaenhammer, T. R., Kleerebezem, M., Kopp, M. V., & Rescigno, M. (2012). The impact of probiotics and prebiotics on the immune system. *Nature Reviews Immunology*, 12(10), 728-734. https://doi.org/10.1038/nri3312

Lai, K. K., Lorca, G. L., & Gonzalez, C. F. (2009). Biochemical Properties of Two Cinnamoyl Esterases Purified from a *Lactobacillus johnsonii* Strain Isolated from Stool Samples of Diabetes-Resistant Rats. *Applied and Environmental Microbiology*, 75(15), 5018-5024. http://doi.org/10.1128/AEM.02837-08

Lorca, G. L., & Valdez, G. F. (2001). A low-pH-inducible, stationary-phase acid tolerance response in *Lactobacillus acidophilus* CRL 639. *Current Microbiology*, 42(1), 21-5. https://doi.org/10.1007/s002840010172

Marty-Teysset, C., de la Torre, F., & Garel, J. (2000). Increased production of hydrogen peroxide by *Lactobacillus delbrueckii* subsp. *bulgaricus* upon aeration: involvement of an NADH oxidase in oxidative stress. *Applied and Environmental Microbiology*, 66(1), 262-7. doi: 10.1128/AEM.66.1.262-267.2000

Nishiyama, K., Nakazato, A., Ueno, S., Seto, Y., Kakuda, T., Takai, S., Yamamoto, Y., & Mukai, T. (2015). Cell surface-associated aggregation-promoting factor from *Lactobacillus gasseri* SBT2055 facilitates host colonization and competitive exclusion of *Campylobacter jejuni*. *Molecular Microbiology*, 98(4), 712-726. doi: 10.1111/mmi.13153.

Nya, E. J. (2015). Development of Probiotics as Biotechnology—Driven Product for Reducing the Incidence of Gastrointestinal Related Disease, 4(9), 2013-2016.

Rajam, R., Kumar, S. B., Prabhasankar, P., & Anandharamakrishnan, C. (2015). Microencapsulation of *Lactobacillus plantarum* MTCC 5422 in fructooligosaccharide and whey protein wall systems and its impact on noodle quality. *Journal of Food Science and Technology*, 52(7), 4029-4041. https://doi.org/10.1007/s3197-014-1506-4

Rodrigues, F. J., Omura, M. H., Cedran, M. F., Dekker, R. F., Barbosa-Dekker, A. M., & Garcia, S. (2017). Effect of natural polymers on the survival of *Lactobacillus casei* encapsulated in alginatemicrospheres. *Journal of Microencapsulation*, 34(5): 431-439. doi: 10.1080/02652048.2017.1343872.

Saarela, M., Virkajärvi, I., Nohynek, L., Vaari, A., & Mättö, J. (2006). Fibres as carriers for *Lactobacillus rhamnosus* during freeze-drying and storage in apple juice and chocolate-coated breakfast cereals. *International Journal of*

*Food Microbiology*, 112(2), 171-8. https://doi.org/10.1016/j.ijfoodmicro.2006.05.019

Sánchez-Rangel, J. C., Benavides, J., Heredia, J. B., Cisneros-Zevallos, L., & Jacobo-Velázquez, D. A. (2013). The Folin-Ciocalteu assay revisited: improvement of its specificity for total phenolic content determination. *Analytical Methods*, 5(21), 5990. https://doi.org/10.1039/c3ay41125g Shiby, V. K., & Mishra, H. N. (2017). Fermented Milks and Milk Products as Functional Foods—A Review Fermented Milks and Milk Products as Functional Foods—A Review, 8398(September). https://doi.org/10.1080/10408398.2010.547398

Valladares, R. B., Graves, C., Wright, K., Gardner, C. L., Lorca, G. L., & Gonzalez, C. F. (2015). H 2 O 2 production rate in *Lactobacillus johnsonii* is modulated via the interplay of a heterodimeric flavin oxidoreductase with a soluble 28 Kd PAS domain containing protein, 6(July), 1-14. https://doi.org/10.3389/fmicb.2015.00716

Valladares, R., Bojilova, L., Potts, A. H., Cameron, E., Gardner, C., Lorca, G., & Gonzalez, C. F. (2013). *Lactobacillus johnsonii* inhibits indoleamine 2,3-dioxygenase and alters tryptophan metabolite levels in BioBreeding rats. *FASEB Journal*, 27(4), 1711-1720. https://doi.org/10.1096/fj.12-223339

Valladares, R., Sankar, D., Li, N., Williams, E., Lai, K. K., Abdelgeliel, A. S., . . . Lorca, G. L. (2010). *Lactobacillus johnsonii* N6.2 mitigates the development of type 1 diabetes in BB-DP rats. *PLoS ONE*, 5(5). https://doi.org/10.1371/journal.pone.0010507 van de Guchte, M., Serror, P., Chervaux, C., Smokvina, T., Ehrlich, S. D., & Maguin, E. (2002). Stress responses in lactic acid bacteria. *Antonie van Leeuwenhoek*, 82(1-4), 187-216. http://dx.doi.org/10.1023/A:1020631532202

Zheng, X., Fu, N., Duan, M., Woo, M. W., Selomulya, C., & Chen, X. D. (2015). The mechanisms of the protective effects of reconstituted skim milk during convective droplet drying of lactic acid bacteria. *Food Research International*, 76, 478-488. https://doi.org/10.1016/j.foodres.2015.07.045

What is claimed is:

1. A unit dose composition comprising a mixture of at least one *Lactobacillus* sp. and a berry extract comprising glucose and fructose, wherein the mixture is lyophilized, and wherein the *Lactobacillus* sp. comprises *Lactobacillus johnsonii* N6.2.

2. A pharmaceutical composition comprising a composition according to claim 1 packaged in a pharmaceutically acceptable vehicle, wherein the pharmaceutically acceptable vehicle comprises a capsule, tablet, suppository, suspension or emulsion.

3. The composition of claim 1, wherein the berry extract is a blueberry extract.

4. The composition of claim 3, wherein the blueberry extract is 1-10% w/v of the composition.

* * * * *